United States Patent
Eickhoff

(10) Patent No.: US 7,640,783 B2
(45) Date of Patent: Jan. 5, 2010

(54) SELF-CALIBRATING GAS DETECTOR AND METHOD

(75) Inventor: Steven J. Eickhoff, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 272 days.

(21) Appl. No.: 11/339,748

(22) Filed: Jan. 25, 2006

(65) Prior Publication Data

US 2006/0266097 A1   Nov. 30, 2006

Related U.S. Application Data

(63) Continuation-in-part of application No. 10/908,737, filed on May 24, 2005, now Pat. No. 7,174,766.

(51) Int. Cl.
    *G01N 33/00* (2006.01)
(52) U.S. Cl. ...................................................... 73/1.06
(58) Field of Classification Search .................. 73/1.02, 73/1.05, 1.06, 1.25
    See application file for complete search history.

(56) References Cited

U.S. PATENT DOCUMENTS

| | | | |
|---|---|---|---|
| 4,322,964 A * | 4/1982 | Melgaard et al. | 73/1.06 |
| 5,092,980 A * | 3/1992 | Maurer et al. | 204/415 |
| 5,741,413 A * | 4/1998 | Capetanopoulos | 205/783 |
| 6,055,840 A | 5/2000 | Warburton | |
| 6,370,940 B2 * | 4/2002 | Warburton | 73/23.21 |
| 2003/0145644 A1 | 8/2003 | Rabbett et al. | |
| 2005/0262924 A1 | 12/2005 | Wood et al. | 73/31.05 |

FOREIGN PATENT DOCUMENTS

GB   2356708   5/2001

OTHER PUBLICATIONS

U.S. Appl. No. 10/908,737, filed May 24, 2005, Steven Eickhoff et al.
PCT International Search Report and Written Opinion from corresponding PCT application, published Jul. 12, 2007.

* cited by examiner

*Primary Examiner*—Daniel S Larkin
(74) *Attorney, Agent, or Firm*—Kris T. Fredrick

(57) ABSTRACT

A portable, calibratible gas detector includes a multi-position gas inflow limiting orifice. When this orifice is in a calibrating position, a source of calibrating gas can be activated to provide a quantity of gas that diffuses into ambient atmosphere flowing through the orifice. The calibration gas can then be sensed.

26 Claims, 2 Drawing Sheets

SELF-CALIBRATING GAS DETECTOR AND METHOD

CROSS REFERENCE TO RELATED APPLICATION

This application is a Continuation-in-Part of U.S. patent application Ser. No. 10/908,737 filed May 24, 2005, now U.S. Pat. No. 7,174,766, entitled "Calibration Device for Carbon Dioxide Sensor."

FIELD OF THE INVENTION

The invention pertains to gas detectors. More particularly, the invention pertains to gas detectors which include a self-calibration function.

BACKGROUND OF THE INVENTION

Gas sensors are known and have been used to sense various gases such as hydrogen, carbon monoxide, carbon dioxide and the like. While known gas sensors are useful and effective for their intended purpose, it has been recognized that at times they can lose sensitivity over time. For example, in connection with electrochemical-type gas sensors, such sensors incorporate a catalytic electrode which is used in connection with detecting gas within the sensor. The activity of that electrode tends to be reduced gradually over time due to contamination and poisoning of the structure. Consequently, the sensitivity of the associated sensor tends to decrease or drift downward. As a result, it is desirable to be able to calibrate such sensors from time to time.

Structures which can generate calibration gases are of interest and have been developed. One such structure is disclosed in previously filed U.S. patent application Ser. No. 10/856,363 filed May 28, 2004, now U.S. Pat. No. 7,037,368, for Calibration Device For Gas Sensors. That application has been assigned to the Assignee hereof and is hereby incorporated by reference. Another such structure has been disclosed in U.S. patent application Ser. No. 10/908,737 previously filed on May 24, 2005, now U.S. Pat. No. 7,174,766, entitled "Calibration Device For Carbon Dioxide Sensor". That application has been assigned to the Assignee hereof and is hereby incorporated by reference.

Beyond an apparatus and a method for generating calibration gas, there continues to be a need for gas sensors which can readily and conveniently calibrated. Preferably such units could be substantially self-contained. It would also be preferable if such units could incorporate a self-calibrating capability without significantly adding to the manufacturing costs, size or weight of such units, especially portable gas detectors.

DETAILED DESCRIPTION

Figure 1:
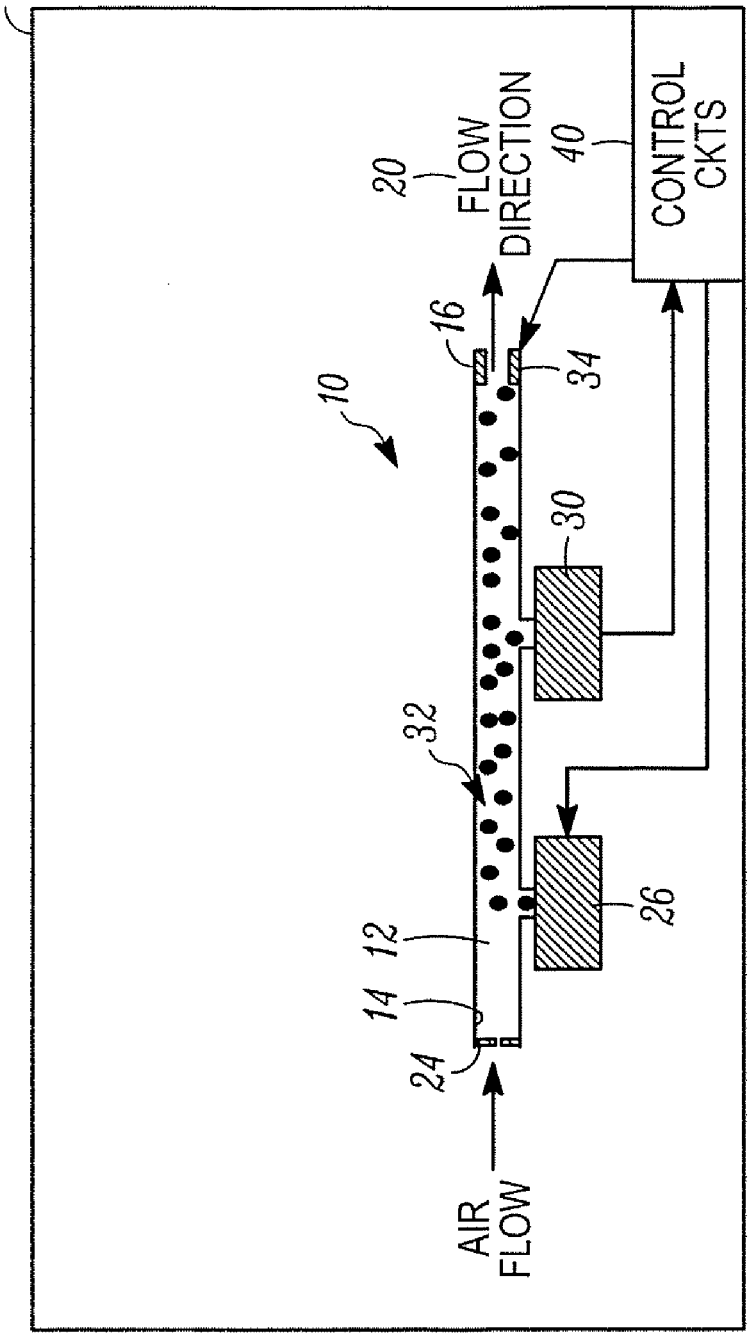
FIG. 1 is a schematic block diagram of a self-calibrating gas detector in accordance with the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

A self-calibrating gas detector which embodies the invention incorporates a flow path with a gas inlet end and an orifice associated therewith. A generator of calibration gas as well as a gas sensor are coupled to the path. Finally, if desired a pump can also be coupled to the path.

In accordance with the invention, to carry out a calibration process, the orifice is moved or switched to a state so that it restricts or constricts the inlet of the flow path. This restricts the flow of ambient atmosphere to the sensor.

The pump and source of calibration gas can both be activated. The pump, when activated, causes ambient atmosphere to pass a sensing region of the gas sensor at a reduced flow rate relative to normal operational flow past the gas sensor. The activated source of calibration gas generates a known amount of the calibration gas.

Those of skill in the art will understand that additional sensors that measure the ambient temperature, humidity, and pressure can be incorporated to further enhance the calibration process since these variables can affect the perceived concentration of a gas. A filter or selectively permeable membrane can also be provided to cover the inlet of the flow path and prevent an inflow of harmful particulates and gasses that might damage the sensor.

The calibration gas diffuses into the inflowing ambient atmosphere traversing the path. This mixture in turn flows into or through the sensing region of the gas sensor. The sensor responds thereto and generates an output signal corresponding thereto which can be used for calibration and making a determination as to the performance characteristics of the sensor.

In accordance with the invention, a reduced flow rate in a range of 1 to 100 cc/min. is particularly advantageous as it reduces the amount of calibration gas required for the process. This can in turn reduce the size and power consumption of the gas generator.

The calibration gas can be generated by any one of a variety of known chemical or electrochemical reactions. For example, a select chemical can be heated until it decomposes. Other forms of gas generation come within the spirit and scope of the invention. Calibration gases can include hydrogen, hydrogen sulfide, carbon dioxide, methane, carbon monoxide and other gases to which the respective sensor will respond.

A detector which embodies the invention is also self-checking. For example, a determination can be made whether the flow path through which the ambient atmosphere is to be drawn is clear or whether it is exhibiting the symptoms of blockage. Further, it is also possible to determine if the sampling pump is functioning as expected.

In yet another aspect of the invention, the flow path can be restricted by a mechanically movable orifice. The orifice could be moved into a calibration position partly closing the inlet which significantly reduces the gas flow through the flow or sampling path. The orifice can be moved into a normal operational position once the calibration process has been concluded.

In another aspect of the invention, the sample pump could be implemented as a peristaltic, diaphragm pump or alternately an electronic pump all without limitation.

FIG. 1 illustrates a gas detector 10 in accordance with the invention. The detector 10 incorporates a flow path 12 with an inlet end 14 and an outlet end 16. In normal operation ambient atmosphere can flow from the inlet end 14 of the flow path 12 through to the outlet end 16 in a direction 20.

The detector 10 can incorporate an orifice 24 which can exhibit at least two different states. In one state the orifice 24 restricts inflowing ambient atmosphere into the flow path 12. In this state, illustrated in FIG. 1, ambient atmosphere can be expected to pass through the flow path 12 at a reduced flow rate relative to normal operation. When not carrying out a calibration function, the orifice 24 can be mechanically slid or rotated from the inlet 14.

Alternately, the orifice 24 can electrically assume a non-constricting state. The non-constricting state can be achieved by means of an electrically actuated transducer which will physically move the orifice 24. The orifice 24 could also be switched electronically from a constricting state to a non-constricting state as would be understood by those of skill in the art.

Detector 10 also incorporates a gas generator 26 and gas sensor 30. The gas sensor 30 can be implemented with any desired technology. It will be understood that the details of the sensor 30 are not limitations of the present invention.

The gas generator 26 can be electrically actuated so as to generate a predetermined quantity of a calibration gas, indicated generally at 32, in the flow path 12. Calibration gas 32 diffuses into the stream of ambient atmosphere flowing in the path 12. A pump 34 can be coupled to outlet 16 to produce a flow of ambient atmosphere and calibration gas 32 through the flow path 12.

Control circuits 40 can be provided to provide electrical signals to actuate the generator 26, receive inputs from the sensor 30 and to actuate pump 34. The detector 10 can be carried in a housing 42 which can also contain a power supply, such as one or more batteries as would be understood by those of skill in the art.

Figure 2:
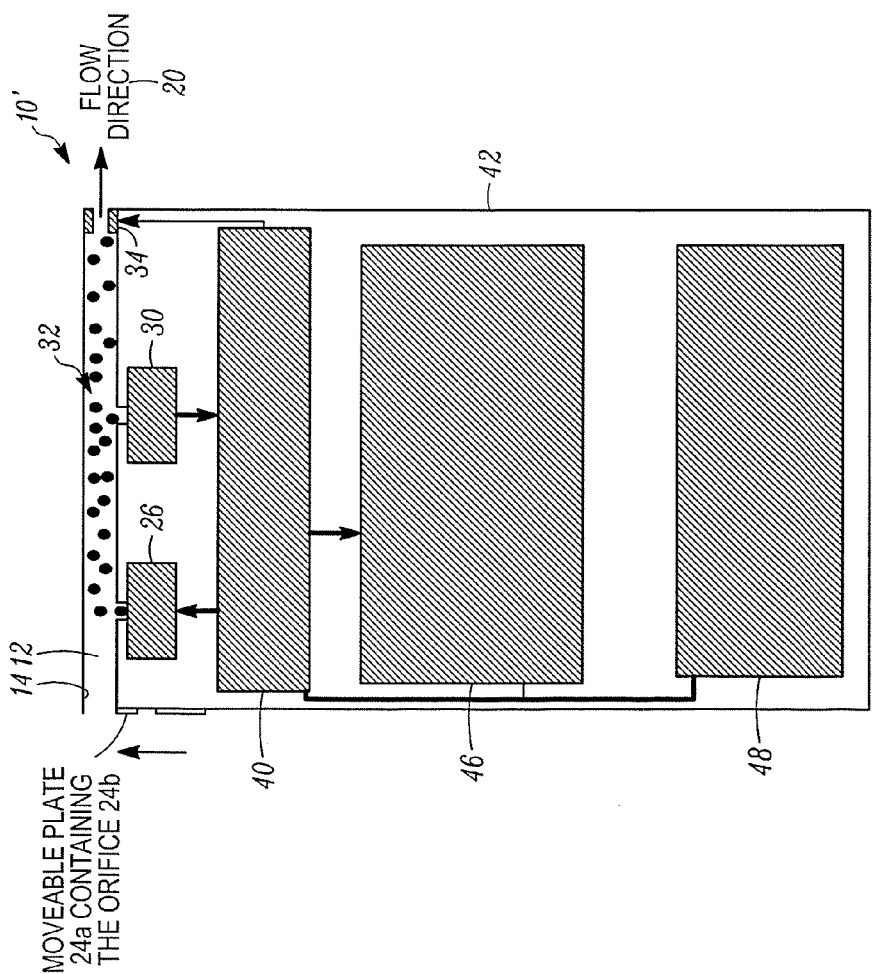
FIG. 2 is a front elevational view of a self-contained, portable, gas detector in accordance with the invention.

FIG. 2 is a front elevational view of a detector 10' which embodies the present invention. Elements of the detector 10' of FIG. 2 which correspond to elements of the detector 10 of FIG. 1 have been assigned the same identification numeral. As illustrated in FIG. 2, in one embodiment of the invention, a movable plate 24a can be provided which has an orifice 24b, best seen in FIG. 3.

The plate 24a is movable in first and second directions, generally indicated at 44 relative to flow path 12. In a calibrating or restricting position the plate 24a partly closes flow path 12. Plate 24a permits an inflow of ambient atmosphere only through the orifice 24b. When in this state, the control electronics 40 can actuate calibration gas generator 26 as well as pump 34 which in turn provides a mixture of ambient atmosphere, drawn through opening 24b, and calibration gas 32 from generator 26. That mixture is presented to gas sensor 30, via path 12. Calibration gas 32 can diffuse into or pass by sensor 30 and be detected thereby.

Outputs from sensor 30 which are coupled to a control electronics 40 provide an electrical signal indicative of the response of the sensor 30 to the calibration gas 32. The electronics 40 can carry out either an automatic or a semi-automatic calibration of the sensor 32 in response to the signals received therefrom.

Figure 3:
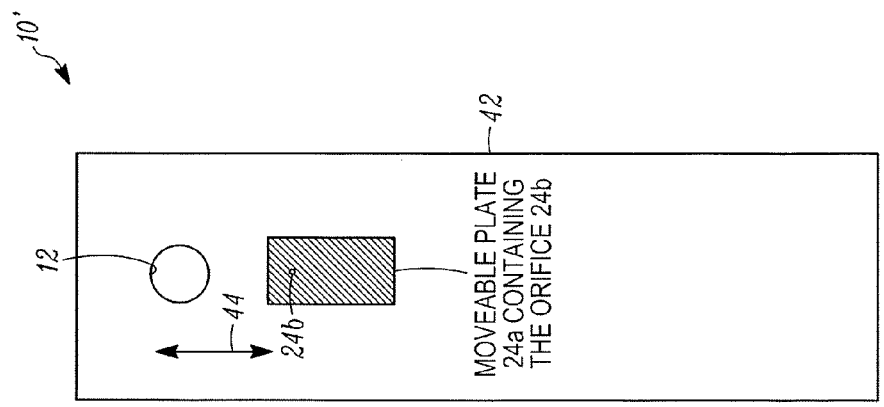
FIG. 3 is a side elevational view of the detector of FIG. 2.

The electronics 40 can actuate display 46 to provide a concentration of the sensed calibration gas if desired. Alternatively, the display 46 can provide an indicium of sensed ambient gas, for example, parts per million, in normal operation where the plate 24b is located in a non-constricting state as illustrated in FIGS. 2 and 3. Power supply 48 can be implemented with rechargeable batteries or replaceable batteries as would be understood by those of skill in the art.

In summary, use of the plate 24a with opening 24b significantly reduces the gas flow through the flow or sampling path 12. This in turn reduces the amount of calibration gas which is needed to achieve a specific concentration. This in turn can reduce the size and power requirements of gas generator 26 as well as power supply 48.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. A system comprising:
a gas sensor having at least one gas flow port, an orifice having at least two states and providing one of calibration flow, or non-calibration flow;
a source of a predetermined calibration gas, the source provides calibration gas when the orifice provides calibration gas flow and which includes an element which promotes a flow of ambient atmosphere into the gas sensor.

2. An apparatus as in claim 1 where the source provides a predetermined quantity of calibration gas.

3. An apparatus as in claim 2 where the calibration gas is selected from a class which includes at least hydrogen, hydrogen sulfide, carbon dioxide, carbon monoxide and methane.

4. An apparatus as in claim 1 where ambient atmosphere which flows into the gas sensor mixes with the calibration gas.

5. An apparatus as in claim 1 where ambient atmosphere which flows into the gas sensor mixes with a predetermined quantity of calibration gas.

6. An apparatus as in claim 1 where the element comprises a gas pump.

7. An apparatus as in claim 1 where the gas sensor includes at least one internal flow path where the source is arranged so that calibration gas enters the flow of ambient atmosphere prior to entering a gas sensing region.

8. An apparatus as in claim 1 where the orifice, in response to a control signal, changes from a state that provides calibration flow to one that provides non-calibration flow.

9. An apparatus as in claim 8 which includes a flow inducing pump.

10. An apparatus as in claim 9 where the gas sensor includes a hollow housing with an internal gas sensing region.

11. An apparatus as in claim 10 where the orifice is in flow communication with the internal gas sensing region.

12. An apparatus as in claim 11 where the pump induces a gas flow through the orifice, past the source, and into the gas sensing region.

13. An apparatus as in claim 12 which includes control circuits coupled at least to the pump and the orifice.

14. An apparatus as in claim 13 where the control circuits are coupled to the source.

15. An apparatus as in claim 14 where the orifice, at least in part, moves from a state that provides calibration flow to one that provides non-calibration flow in response to at least one signal from the control circuits.

16. An apparatus as in claim 14 where the control circuits activate the source to provide calibration gas.

17. An apparatus as in claim 16 where the source provides a predetermined quantity of calibration gas.

18. A calibratable gas detector comprising:
a housing, the housing including at least one gas inflow port with an internal gas flow path coupled thereto;
a source of calibration gas in flow communication with the gas flow path;
a gas sensor where ambient atmosphere drawn through the gas inflow port flows into the gas sensor;

a pump coupled to the gas flow path; and a multi-state orifice coupled to the inflow port, the orifice having a constricting state which limits flow into the flow path and a second, different state.

19. A detector as in claim 18 which includes control circuits to switch the orifice between states.

20. A detector as in claim 18 where control circuits activate the source to provide calibration gas while the orifice is in a constricting state.

21. A detector as in claim 20 where the pump is activated at least while the source is activated.

22. A detector as in claim 18 where the orifice is movable between states.

23. A detector as in claim 22 where the orifice is manually movable between states.

24. A detector as in claim 23 which includes a manually operable control member to activate the source thereby producing the calibration gas.

25. A calibratable gas detector comprising:

an internal gas flow path coupled to at least one gas inflow port, ambient air drawn through the gas inflow port and flowing through the gas flow path;

an orifice coupled to the gas inflow port, the orifice having at least a calibration flow state and an non-calibration flow state;

a source of a predetermined amount of a calibration gas, the source in flow communication with the gas flow path, the source providing calibration gas when the orifice is in the calibration flow state, the calibration gas diffusing into the ambient atmosphere in the gas flow path; and a sensor, the calibration gas and the ambient atmosphere flowing into the sensor, the sensor sensing a concentration of the calibration gas.

26. A calibratable gas detector as in claim 25 which includes a flow inducing pump.

* * * * *